United States Patent
Tyber et al.

(10) Patent No.: US 8,303,589 B2
(45) Date of Patent: Nov. 6, 2012

(54) FIXATION SYSTEM, AN INTRAMEDULLARY FIXATION ASSEMBLY AND METHOD OF USE

(75) Inventors: Jeff Tyber, Bethlehem, PA (US); Jamy Gannoe, West Milford, NJ (US); Chris Digiovanni, Barrington, RI (US)

(73) Assignee: Extremity Medical LLC, Parsippany, NJ (US)

( * ) Notice: Subject to any disclaimer, the term of this patent is extended or adjusted under 35 U.S.C. 154(b) by 266 days.

(21) Appl. No.: 12/456,808

(22) Filed: Jun. 23, 2009

(65) Prior Publication Data
US 2010/0121324 A1 May 13, 2010

Related U.S. Application Data

(60) Provisional application No. 61/132,932, filed on Jun. 24, 2008.

(51) Int. Cl.
*A61B 17/56* (2006.01)
(52) U.S. Cl. ............. 606/62; 606/64; 606/86 R; 606/96; 606/301
(58) Field of Classification Search ................ 606/54, 606/62, 80, 96
See application file for complete search history.

(56) References Cited

U.S. PATENT DOCUMENTS

| | | |
|---|---|---|
| 928,997 A | 7/1909 | Muller |
| 2,398,220 A | 4/1946 | Gelpcke |
| 2,580,821 A | 1/1952 | Nicola |
| 3,019,686 A | 2/1962 | Behrle |
| 3,200,694 A | 8/1965 | Rapata |
| 3,411,398 A | 11/1968 | Blakeley et al. |
| 3,474,537 A | 10/1969 | Christensen |
| 3,924,276 A | 12/1975 | Eaton |
| 4,152,533 A | 5/1979 | Gazda |
| 4,381,770 A * | 5/1983 | Neufeld ................. 606/67 |
| 4,465,065 A * | 8/1984 | Gotfried ................ 606/65 |
| 4,760,843 A | 8/1988 | Fischer et al. |
| 4,795,294 A | 1/1989 | Takada et al. |
| 4,854,797 A | 8/1989 | Gourd |
| 4,930,963 A | 6/1990 | Rockenfeller et al. |
| 4,940,467 A | 7/1990 | Tronzo |
| 4,947,502 A | 8/1990 | Engelhardt |
| 4,987,714 A | 1/1991 | Lemke |
| 5,084,050 A | 1/1992 | Draenert |
| 5,112,333 A | 5/1992 | Fixel |
| 5,163,940 A * | 11/1992 | Bourque .............. 606/96 |
| 5,209,753 A | 5/1993 | Biedermann |
| 5,350,380 A * | 9/1994 | Goble et al. ........... 606/80 |
| 5,403,321 A * | 4/1995 | DiMarco .............. 606/96 |
| 5,454,267 A | 10/1995 | Moreau et al. |
| 5,456,267 A | 10/1995 | Stark |

(Continued)

FOREIGN PATENT DOCUMENTS
WO    WO 2006116164    11/2006

(Continued)

*Primary Examiner* — Eduardo C Robert
*Assistant Examiner* — Stuart S Bray
(74) *Attorney, Agent, or Firm* — Ward & Zinna, LLC

(57) ABSTRACT

A fixation system, including an intramedullary fixation assembly and an instrument for coupling the intramedullary fixation assembly to bones. The intramedullary fixation assembly includes a proximal screw member positioned at a proximal end of the intramedullary fixation assembly, a distal member positioned at a distal end of the intramedullary fixation assembly, where the proximal screw member is slideably coupled to the distal member and makes a fixed angle with the distal member.

60 Claims, 8 Drawing Sheets

U.S. PATENT DOCUMENTS

| | | | |
|---|---|---|---|
| 5,478,341 A * | 12/1995 | Cook et al. | 606/62 |
| 5,501,557 A | 3/1996 | Wakai | |
| 5,505,731 A | 4/1996 | Tornier | |
| 5,531,748 A | 7/1996 | de la Caffiniere | |
| 5,540,694 A * | 7/1996 | DeCarlo et al. | 606/80 |
| 5,573,538 A * | 11/1996 | Laboureau | 606/96 |
| 5,601,550 A * | 2/1997 | Esser | 606/54 |
| 5,613,971 A * | 3/1997 | Lower et al. | 606/96 |
| 5,620,449 A * | 4/1997 | Faccioli et al. | 606/98 |
| 5,702,470 A | 12/1997 | Menon | |
| 5,718,705 A | 2/1998 | Sammarco | |
| 5,718,706 A | 2/1998 | Roger | |
| 5,741,266 A * | 4/1998 | Moran et al. | 606/96 |
| 5,766,221 A * | 6/1998 | Benderev et al. | 606/232 |
| 5,779,704 A | 7/1998 | Kim | |
| 5,857,816 A | 1/1999 | Assmundson | |
| 5,865,559 A | 2/1999 | Yang | |
| 5,888,203 A | 3/1999 | Goldberg | |
| 5,891,150 A * | 4/1999 | Chan | 606/96 |
| 5,968,050 A * | 10/1999 | Torrie | 606/87 |
| 5,984,681 A | 11/1999 | Huang | |
| 5,997,541 A | 12/1999 | Schenk | |
| D420,132 S * | 2/2000 | Bucholz et al. | D24/140 |
| 6,019,761 A | 2/2000 | Gustillo | |
| 6,030,162 A | 2/2000 | Huebner | |
| 6,048,343 A | 4/2000 | Mathis et al. | |
| 6,106,528 A | 8/2000 | Durham et al. | |
| 6,120,511 A * | 9/2000 | Chan | 606/96 |
| 6,123,709 A | 9/2000 | Jones | |
| 6,123,711 A | 9/2000 | Winters | |
| 6,126,661 A * | 10/2000 | Faccioli et al. | 606/64 |
| 6,168,595 B1 | 1/2001 | Durham et al. | |
| 6,168,597 B1 | 1/2001 | Biedermann et al. | |
| 6,174,119 B1 | 1/2001 | Orr | |
| 6,214,007 B1 | 4/2001 | Anderson | |
| 6,214,012 B1 | 4/2001 | Karpman et al. | |
| 6,221,074 B1 | 4/2001 | Cole et al. | |
| 6,235,031 B1 | 5/2001 | Hodgeman et al. | |
| 6,247,883 B1 | 6/2001 | Monserratt | |
| 6,254,605 B1 * | 7/2001 | Howell | 606/96 |
| 6,254,606 B1 * | 7/2001 | Carney et al. | 606/102 |
| 6,261,039 B1 | 7/2001 | Reed | |
| 6,261,290 B1 | 7/2001 | Friedl | |
| 6,270,499 B1 | 8/2001 | Leu et al. | |
| 6,280,442 B1 | 8/2001 | Barker et al. | |
| 6,287,313 B1 * | 9/2001 | Sasso | 606/96 |
| 6,379,362 B1 | 4/2002 | Birk et al. | |
| 6,402,753 B1 | 6/2002 | Cole et al. | |
| 6,402,757 B1 | 6/2002 | Moore et al. | |
| 6,423,064 B1 | 7/2002 | Kluger | |
| 6,435,788 B2 | 8/2002 | Reed | |
| 6,443,954 B1 | 9/2002 | Bramlet et al. | |
| 6,458,134 B1 | 10/2002 | Songer et al. | |
| 6,517,541 B1 | 2/2003 | Sesic | |
| 6,527,775 B1 | 3/2003 | Warburton | |
| 6,562,046 B2 * | 5/2003 | Sasso | 606/96 |
| 6,569,165 B2 | 5/2003 | Wahl et al. | |
| 6,589,245 B1 | 7/2003 | Weiler et al. | |
| 6,596,008 B1 | 7/2003 | Kambin | |
| 6,626,916 B1 | 9/2003 | Yeung et al. | |
| 6,629,976 B1 | 10/2003 | Gnos et al. | |
| 6,632,057 B1 | 10/2003 | Fauchet | |
| 6,634,844 B2 | 10/2003 | Huber | |
| 6,648,889 B2 | 11/2003 | Bramlet et al. | |
| 6,669,700 B1 | 12/2003 | Farris et al. | |
| 6,679,888 B2 * | 1/2004 | Green et al. | 606/86 R |
| 6,685,706 B2 | 2/2004 | Padget et al. | |
| 6,692,496 B1 | 2/2004 | Wardlaw | |
| 6,692,503 B2 * | 2/2004 | Foley et al. | 606/96 |
| 6,695,844 B2 | 2/2004 | Bramlet et al. | |
| 6,709,436 B1 | 3/2004 | Hover et al. | |
| 6,712,849 B2 * | 3/2004 | Re et al. | 623/13.14 |
| 6,743,018 B1 | 6/2004 | Morrow | |
| 6,778,861 B1 | 8/2004 | Liebrecht et al. | |
| 6,793,659 B2 | 9/2004 | Putnam | |
| 6,808,527 B2 | 10/2004 | Lower et al. | |
| 6,849,093 B2 | 2/2005 | Michelson | |
| 6,875,216 B2 | 4/2005 | Wolf | |
| 6,908,271 B2 | 6/2005 | Breslin et al. | |
| 6,951,538 B2 * | 10/2005 | Ritland | 600/210 |
| 6,951,561 B2 | 10/2005 | Warren et al. | |
| 6,981,974 B2 | 1/2006 | Berger | |
| 7,018,380 B2 | 3/2006 | Cole | |
| 7,037,309 B2 | 5/2006 | Weil et al. | |
| 7,041,104 B1 | 5/2006 | Cole et al. | |
| 7,063,724 B2 * | 6/2006 | Re et al. | 623/13.14 |
| 7,074,221 B2 | 7/2006 | Michelson | |
| 7,144,399 B2 * | 12/2006 | Hayes et al. | 606/98 |
| 7,160,302 B2 | 1/2007 | Warburton | |
| 7,175,632 B2 * | 2/2007 | Singhatat et al. | 606/98 |
| 7,229,448 B2 | 6/2007 | Goble et al. | |
| 7,232,442 B2 | 6/2007 | Sohngen et al. | |
| 7,247,156 B2 | 7/2007 | Ekholm et al. | |
| 7,267,678 B2 | 9/2007 | Medoff | |
| 7,326,248 B2 | 2/2008 | Michelson | |
| 7,331,962 B2 | 2/2008 | Branemark | |
| 7,341,588 B2 | 3/2008 | Swanson | |
| 7,344,538 B2 | 3/2008 | Myerson et al. | |
| 7,410,488 B2 | 8/2008 | Janna et al. | |
| 7,524,326 B2 | 4/2009 | Dierks | |
| 7,527,627 B2 | 5/2009 | Ferrante et al. | |
| 7,582,107 B2 | 9/2009 | Trail et al. | |
| 7,588,577 B2 | 9/2009 | Fencl et al. | |
| 7,591,819 B2 | 9/2009 | Zander | |
| 7,601,153 B2 | 10/2009 | Shinjo et al. | |
| 7,608,097 B2 | 10/2009 | Kyle | |
| 7,632,272 B2 | 12/2009 | Munro et al. | |
| 7,655,009 B2 | 2/2010 | Grusin | |
| 7,666,212 B2 | 2/2010 | Pathak | |
| 7,670,340 B2 | 3/2010 | Brivio et al. | |
| 7,713,271 B2 | 5/2010 | Warburton | |
| 7,717,947 B1 | 5/2010 | Wilberg et al. | |
| 7,731,721 B2 * | 6/2010 | Rathbun et al. | 606/96 |
| 7,731,738 B2 | 6/2010 | Jackson et al. | |
| 7,763,021 B2 | 7/2010 | Cole et al. | |
| 7,763,022 B2 | 7/2010 | Speitling et al. | |
| 7,763,023 B2 | 7/2010 | Gotfried | |
| 7,771,428 B2 * | 8/2010 | Siravo et al. | 606/62 |
| 7,785,326 B2 | 8/2010 | Green et al. | |
| 7,794,483 B2 | 9/2010 | Capanni | |
| 7,799,061 B2 | 9/2010 | Kay et al. | |
| 7,815,646 B2 * | 10/2010 | Hart | 606/96 |
| 7,842,036 B2 | 11/2010 | Phillips | |
| 7,867,231 B2 | 1/2011 | Cole | |
| 7,892,234 B2 | 2/2011 | Schlienger et al. | |
| 7,892,264 B2 | 2/2011 | Sanders et al. | |
| 7,909,825 B2 | 3/2011 | Saravia et al. | |
| 7,914,532 B2 | 3/2011 | Shaver et al. | |
| 7,918,853 B2 | 4/2011 | Watanabe et al. | |
| 7,922,748 B2 | 4/2011 | Hoffman | |
| 7,927,340 B2 * | 4/2011 | Hart | 606/96 |
| 7,938,848 B2 | 5/2011 | Sweeney | |
| 7,947,043 B2 | 5/2011 | Mutchler | |
| 8,034,056 B2 | 10/2011 | Fencl et al. | |
| 8,034,082 B2 | 10/2011 | Lee et al. | |
| 8,057,476 B2 | 11/2011 | Ekholm et al. | |
| 8,092,453 B2 | 1/2012 | Warburton | |
| 8,100,910 B2 | 1/2012 | Warburton | |
| 8,100,946 B2 | 1/2012 | Strausbaugh et al. | |
| 8,206,424 B2 | 6/2012 | Biedermann et al. | |
| 2001/0021852 A1 | 9/2001 | Chappius | |
| 2002/0052605 A1 | 5/2002 | Grooms et al. | |
| 2002/0218712 | 9/2002 | Michelson | |
| 2002/0143333 A1 * | 10/2002 | von Hoffmann et al. | 606/67 |
| 2002/0169453 A1 | 11/2002 | Berger | |
| 2002/0197134 A1 | 12/2002 | Huber | |
| 2003/0028193 A1 | 2/2003 | Weil et al. | |
| 2003/0060827 A1 | 3/2003 | Coughln | |
| 2003/0065391 A1 * | 4/2003 | Re et al. | 623/13.14 |
| 2003/0083667 A1 * | 5/2003 | Ralph et al. | 606/96 |
| 2003/0147716 A1 | 8/2003 | Nagawa | |
| 2003/0158555 A1 | 8/2003 | Sanders | |
| 2003/0229346 A1 | 12/2003 | Oribe et al. | |
| 2004/0006345 A1 | 1/2004 | Vlahos et al. | |
| 2004/0082959 A1 * | 4/2004 | Hayes et al. | 606/96 |
| 2004/0097945 A1 | 5/2004 | Wolf | |
| 2004/0172031 A1 | 9/2004 | Rubecamp et al. | |

| | | |
|---|---|---|
| 2004/0181234 A1 | 9/2004 | McDevitt et al. |
| 2004/0220570 A1 | 11/2004 | Frigg |
| 2005/0015092 A1* | 1/2005 | Rathbun et al. ............... 606/96 |
| 2005/0069397 A1 | 3/2005 | Shavit et al. |
| 2005/0107791 A1 | 5/2005 | Manderson |
| 2005/0125070 A1 | 6/2005 | Reiley |
| 2005/0149030 A1 | 7/2005 | Serhan et al. |
| 2005/0171544 A1 | 8/2005 | Falkner, Jr. |
| 2005/0171546 A1 | 8/2005 | Wolf |
| 2005/0192580 A1 | 9/2005 | Dalton |
| 2005/0251147 A1 | 11/2005 | Novak |
| 2005/0273101 A1 | 12/2005 | Schumacher |
| 2005/0277940 A1 | 12/2005 | Neff |
| 2005/0283159 A1 | 12/2005 | Amara |
| 2006/0009774 A1* | 1/2006 | Goble et al. ............... 606/85 |
| 2006/0009846 A1 | 1/2006 | Trieu et al. |
| 2006/0015101 A1 | 1/2006 | Warburton et al. |
| 2006/0052787 A1 | 3/2006 | Re et al. |
| 2006/0095039 A1 | 5/2006 | Mutchler |
| 2006/0122600 A1 | 6/2006 | Cole |
| 2006/0122612 A1 | 6/2006 | Justin et al. |
| 2006/0142770 A1 | 6/2006 | Capanni |
| 2006/0149244 A1 | 7/2006 | Amrein et al. |
| 2006/0173461 A1 | 8/2006 | Kay et al. |
| 2006/0189991 A1 | 8/2006 | Bickley |
| 2006/0200143 A1 | 9/2006 | Warburton |
| 2006/0200144 A1 | 9/2006 | Warburton |
| 2006/0200160 A1 | 9/2006 | Border et al. |
| 2006/0206044 A1 | 9/2006 | Simon |
| 2006/0235396 A1 | 10/2006 | Sanders et al. |
| 2006/0241608 A1 | 10/2006 | Myerson et al. |
| 2006/0241777 A1 | 10/2006 | Partin et al. |
| 2006/0264954 A1 | 11/2006 | Sweeney, II et al. |
| 2007/0021839 A1 | 1/2007 | Lowe |
| 2007/0038306 A1 | 2/2007 | O'Gara |
| 2007/0055286 A1* | 3/2007 | Ralph et al. ............... 606/96 |
| 2007/0066977 A1* | 3/2007 | Assell et al. ............... 606/96 |
| 2007/0073290 A1 | 3/2007 | Boehm, Jr. |
| 2007/0093841 A1* | 4/2007 | Hoogland ............... 606/80 |
| 2007/0112432 A1 | 5/2007 | Reiley |
| 2007/0173835 A1 | 7/2007 | Medoff |
| 2007/0233114 A1 | 10/2007 | Bouman |
| 2007/0270848 A1 | 11/2007 | Lin |
| 2007/0270855 A1 | 11/2007 | Partin |
| 2008/0065224 A1 | 3/2008 | Reigstad et al. |
| 2008/0091203 A1 | 4/2008 | Warburton et al. |
| 2008/0154271 A1* | 6/2008 | Berberich et al. ............... 606/88 |
| 2008/0208261 A1 | 8/2008 | Medoff |
| 2008/0221623 A1 | 9/2008 | Gooch |
| 2008/0269908 A1 | 10/2008 | Warburton |
| 2008/0279654 A1 | 11/2008 | Deschamps |
| 2008/0294164 A1 | 11/2008 | Frank et al. |
| 2008/0306487 A1* | 12/2008 | Hart ............... 606/96 |
| 2008/0306537 A1 | 12/2008 | Culbert |
| 2009/0018542 A1 | 1/2009 | Saravia et al. |
| 2009/0048600 A1 | 2/2009 | Matityahu et al. |
| 2009/0062797 A1* | 3/2009 | Huebner et al. ............... 606/62 |
| 2009/0088767 A1* | 4/2009 | Leyden et al. ............... 606/96 |
| 2009/0088804 A1* | 4/2009 | Kyle et al. ............... 606/280 |
| 2009/0088806 A1 | 4/2009 | Leyden et al. |
| 2009/0093813 A1* | 4/2009 | Elghazaly ............... 606/62 |
| 2009/0093849 A1 | 4/2009 | Grabowski |
| 2009/0093851 A1 | 4/2009 | Osman |
| 2009/0099571 A1* | 4/2009 | Cresina et al. ............... 606/96 |
| 2009/0149857 A1* | 6/2009 | Culbert et al. ............... 606/80 |
| 2009/0157077 A1 | 6/2009 | Larsen et al. |
| 2009/0157078 A1 | 6/2009 | Mikol |
| 2009/0157079 A1 | 6/2009 | Warburton et al. |
| 2009/0157080 A1 | 6/2009 | Warburton |
| 2009/0177203 A1 | 7/2009 | Reiley |
| 2009/0198289 A1 | 8/2009 | Manderson |
| 2009/0209961 A1 | 8/2009 | Ferrante et al. |
| 2009/0240252 A1* | 9/2009 | Chang ............... 606/96 |
| 2009/0248025 A1 | 10/2009 | Haidukewych et al. |
| 2009/0264885 A1 | 10/2009 | Grant et al. |
| 2009/0281580 A1 | 11/2009 | Emannuel |
| 2009/0292292 A1 | 11/2009 | Fencl et al. |
| 2009/0306666 A1 | 12/2009 | Czartoski et al. |
| 2010/0023011 A1 | 1/2010 | Nakamura |
| 2010/0023064 A1 | 1/2010 | Brunger et al. |
| 2010/0030280 A1 | 2/2010 | Jackson |
| 2010/0042164 A1 | 2/2010 | Lee et al. |
| 2010/0042167 A1 | 2/2010 | Nebosky et al. |
| 2010/0057141 A1 | 3/2010 | Abdelgany et al. |
| 2010/0069970 A1 | 3/2010 | Lewis et al. |
| 2010/0076499 A1 | 3/2010 | Mcnamara et al. |
| 2010/0179551 A1 | 7/2010 | Keller et al. |
| 2010/0256638 A1* | 10/2010 | Tyber et al. ............... 606/62 |
| 2010/0312279 A1 | 12/2010 | Gephart et al. |
| 2010/0324556 A1* | 12/2010 | Tyber et al. ............... 606/62 |
| 2011/0004255 A1* | 1/2011 | Weiner et al. ............... 606/301 |
| 2011/0022066 A1 | 1/2011 | Sevrain |
| 2011/0060337 A1 | 3/2011 | Ferrante et al. |
| 2011/0144645 A1 | 6/2011 | Saravia et al. |
| 2011/0213367 A1* | 9/2011 | Tyber et al. ............... 606/62 |
| 2011/0218580 A1 | 9/2011 | Schwager et al. |
| 2011/0282398 A1 | 11/2011 | Overes et al. |
| 2011/0301651 A1 | 12/2011 | Kirschman |
| 2012/0004690 A1 | 1/2012 | Gonzalez-Hernandez |
| 2012/0010669 A1 | 1/2012 | O'Neil et al. |
| 2012/0016424 A1 | 1/2012 | Kave |
| 2012/0022603 A1 | 1/2012 | Kirschman |
| 2012/0095516 A1 | 4/2012 | Dikeman |
| 2012/0109213 A1 | 5/2012 | Appenzeller et al. |

FOREIGN PATENT DOCUMENTS

WO    WO 2007131287    11/2007

* cited by examiner

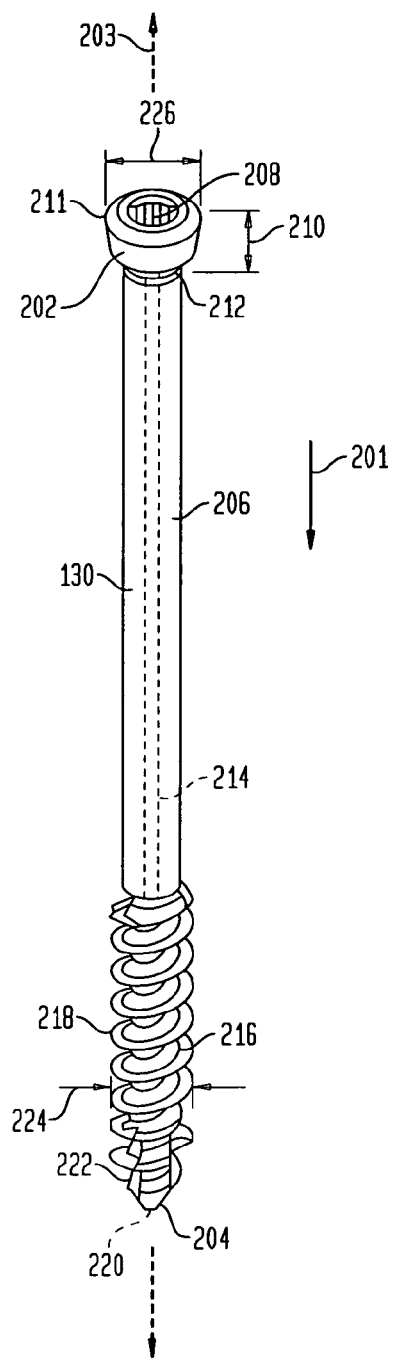

FIXATION SYSTEM, AN INTRAMEDULLARY FIXATION ASSEMBLY AND METHOD OF USE

CROSS-REFERENCE TO RELATED APPLICATION

This application claims the benefit of Provisional Application No. 61/132,932, filed Jun. 24, 2008, the entire contents of which are herein incorporated by reference.

FIELD OF THE INVENTION

This invention relates to the field of orthopedic implant devices, and more particularly, to an intramedullary fixation assembly used for internal fixation of angled joints, bones and deformity correction, such as the bones in the foot.

BACKGROUND OF THE INVENTION

Orthopedic implant devices, such as intramedullary nails, plates, rods and screws are often used to repair or reconstruct bones and joints affected by trauma, degeneration, deformity and disease, such as Charcot arthropathy caused by diabetes in some patients. Charcot arthropathy (or Charcot foot) is a destructive process affecting many regions including joints of the foot and ankle in diabetics. This condition causes bony fragmentation, dislocation, and fractures that eventually progresses to foot deformity, bony prominences, ulceration and instability of the foot. Charcot arthropathy can affect any joint in the body but is often seen in the feet affecting the metatarsal, tarsometatarsal and tarsal joints and frequently causes the foot to lose its arch or curvature, thus resulting in "flat footedness" in the mid-foot region.

Early treatment for Charcot foot includes the use of therapeutic footwear, immobilization of the foot and/or non-weight bearing treatment. Surgical treatments include orthopedic fixation devices that fixate the bones in order to fuse them into a stable mass. These orthopedic implant devices realign bone segments and hold them together in compression until healing occurs, resulting in a stable mass.

Various implants have been utilized for surgical treatment, including bone screws. While these devices allow fixation and promote fusion, they do not deliver restoration of the arch in a Charcot foot. Instead, the physician must estimate the arch and manually align the bones and deliver the screws to hold the bones in place, while reducing bone purchase. Intramedullary nails and/or a plate with a lag screw too have deficiencies. These intramedullary nails also do not reconstruct an arch that is lost due to Charcot foot disease.

Moreover, infections and wound complications are a major concern in aforementioned procedures. Wound closure is technically demanding for the surgeon, and devices that add surface prominence, such as plates or exposed screws, add to the difficulty by requiring greater tissue tension during incision reapproximation. This increases the risk of postoperative wound infections and dehiscence that may ultimately result in limb amputation.

There is therefore a need for an intramedullary fixation assembly and method of use that overcomes some or all of the previously delineated drawbacks of prior fixation assemblies.

SUMMARY OF THE INVENTION

An object of the present invention is to overcome the drawbacks of previous inventions.

Another object of the present invention is to provide a novel and useful intramedullary fixation assembly that may be utilized to treat any bones in human body.

Another object of the present invention is to provide a novel and useful intramedullary fixation assembly that may be utilized to treat bones in a mid-foot region.

Another object of the present invention is to restore the arch by utilizing an intramedullary assembly.

Another object of the present invention is to provide a system for treating deteriorating bones in a mid-foot region.

Another object of the present invention is to provide a method for restoring the arch of the foot by delivering a fixator that can be coupled in a patient's foot.

In a first non-limiting aspect of the present invention, a fixation assembly comprising two members is provided. A first member, positioned at a proximal end of the fixation assembly, has an elongated portion and a tapered bulbous end. A second member, positioned at a distal end of the fixation assembly, has an internal tapered aperture, wherein the elongated portion resides within the internal tapered aperture. The first member forms a fixed angle with the second member, thereby selectively coupling the first member to the second member.

In a second non-limiting aspect of the present invention, a method for reconstructing an arch in a mid-foot region comprises eight steps. Step one includes making an incision in the mid-foot region of a patient's foot. Step two includes gun-stocking the foot to expose the articular surface. Step three includes reaming the intramedullary canal and inserting a distal member. Step four includes coupling the instrument to the distal member. Step five includes assessing the position of the proximal member with a guide wire. Step six includes pre-drilling a hole through the joints selected for fusion. The seventh step includes inserting the proximal member over the guide wire until rigid connection with the tapered aperture is made that compresses the joint and wherein the proximal member is at an angle to the distal member. The eighth step includes removing the instrument and closing the incision, thereby causing the arch to be formed in the mid-foot region.

In a third non-limiting aspect of the present invention, an instrument is combined with a fixation assembly for reconstructing an arch in a mid-foot region. The instrument has a handle, a "U-shaped" recess having two sides and a tapered bore. The intramedullary fixation assembly has a first member and a second member. The first member is positioned at a proximal end of the intramedullary fixation assembly. The first member has an elongated portion and a bulbous portion. The second member is positioned at a distal end of the intramedullary fixation assembly. The second member has an internal tapered aperture, a plurality of grooves and a threaded portion. The elongated portion resides within the internal tapered aperture, and a "U-shaped" recess having two sides that couple the first member to the second member, and further coupling the instrument to the intramedullary fixation assembly for reconstructing the arch in the mid-foot region.

BRIEF DESCRIPTION OF THE DRAWINGS

A further understanding of the present invention can be obtained by reference to a preferred embodiment set forth in the illustrations of the accompanying drawings. Although the illustrated embodiment is merely exemplary of systems and methods for carrying out the present invention, both the organization and method of operation of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

For a more complete understanding of the present invention, reference is now made to the following drawings in which:

FIG. 2 is a perspective view of a proximal screw member used in the fixation system shown in FIG. 1 according to the preferred embodiment of the present invention.

DETAILED DESCRIPTION

The present invention may be understood more readily by reference to the following detailed description of preferred embodiment of the invention. However, techniques, systems and operating structures in accordance with the present invention may be embodied in a wide variety of forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein, which define the scope of the present invention. It must be noted that, as used in the specification and the appended claims, the singular forms "a", "an", and "the" include plural referents unless the context clearly indicates otherwise.

Figure 1:
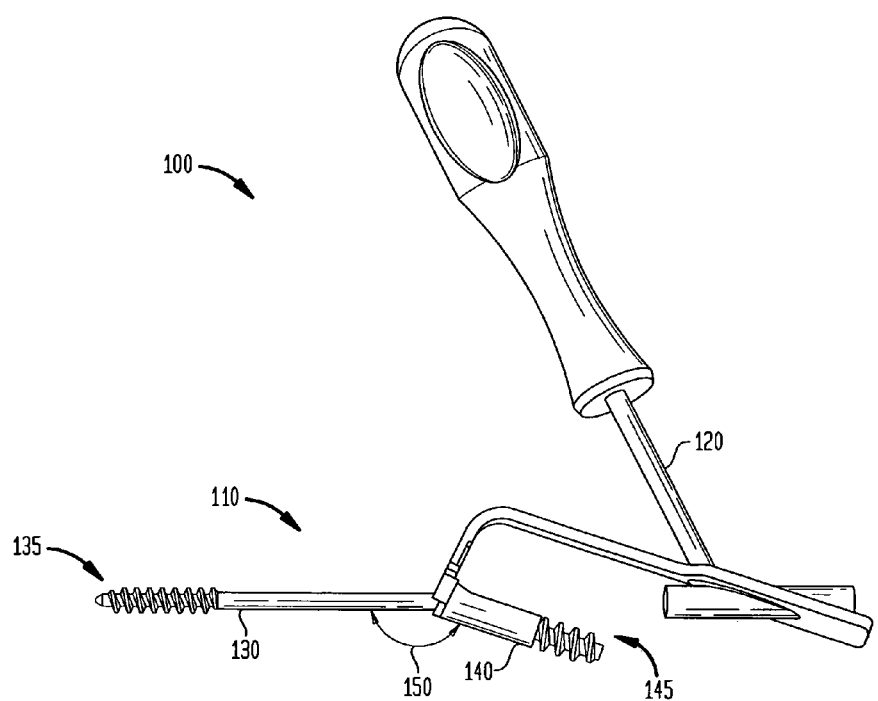
FIG. 1 is a perspective view of a fixation system according to a preferred embodiment of the present invention.

Referring now to FIG. 1, there is shown a fixation system 100 which is made in accordance with the teachings of the preferred embodiment of the invention. As shown, the fixation system 100 includes an intramedullary fixation assembly 110, comprising a proximal screw member 130 and a distal member 140. Proximal screw member 130 is provided on proximal end 135 of assembly 110 and is coupled to a distal member 140 that is provided on the distal end 145 of the fixation assembly 110. Also, proximal screw member 130 makes a fixed angle 150 with distal member 140 and this angle 150 determines the angle for arch restoration. Moreover, fixation system 100 includes instrument 120 that is utilized to couple intramedullary fixation assembly 110 to the bones, in one non-limiting example, in the mid-foot region (not shown). It should be appreciated that in one non-limiting embodiment, intramedullary fixation assembly 110 may be made from a Titanium material, although, in other non-limiting embodiments, intramedullary fixation assembly 110 may be made from SST; PEEK, NiTi, Cobalt chrome or other similar types of materials. It should also be appreciated that intramedullary fixation assembly 110 may be utilized for the internal fixation of other bones in the human body.

As shown in FIG. 2, proximal screw member 130 is generally cylindrical in shape and extends from first bulbous portion 202 to second tapered end 204. End 204 has a diameter that is slightly smaller than diameter 226 of bulbous portion 202. Additionally, bulbous portion 202 has a taper, such as a Morse taper, with a width that decreases from end 211 to end 212. The taper allows for a locked interference fit with tapered aperture 316 when tapered bulbous portion 202 is combined with tapered aperture 316, shown and described below. Moreover, bulbous portion 202 is generally circular and has a generally hexagonal torque transmitting aperture 208 that traverses length 210 of bulbous portion 202. However, a star-shaped aperture, a square-shaped aperture, or any other shaped aperture may be utilized without departing from the scope of the present invention. Torque transmitting aperture 208 is utilized to transmit a torque from bulbous portion 202 to tapered end 204 by rotating bulbous portion 202.

Further, proximal screw member 130 has a first smooth exterior portion 206 extending from end 212 of bulbous portion 202. Portion 206 comprises an internal aperture 214 that longitudinally traverses portion 206 in direction 201. Portion 206 terminates into a second generally tubular portion 216. Portion 216 may comprise internal circular aperture 220 that longitudinally traverses inside portion 216. Internal circular aperture 220 is aligned with apertures 214 and 208 along axis 203 to form a continuous opening (i.e., a cannula) from bulbous portion 202 to end 204. The continuous opening or cannula is provided to interact with a guide wire (not shown) by receiving the guide wire within the continuous opening thereby positioning and locating the proximal member 130. In other non-limiting embodiments, the proximal member 130 may be provided without apertures 220 and 214 (i.e., the proximal member is solid).

Furthermore, tubular portion 216 has a plurality of circular threads, such as threads 218, which are circumferentially disposed on the external surface of portion 216 and, with threads 218 having an external diameter 224. Portion 216 may also be provided with a self-tapping leading edge 222 to provide portion 216 with the ability to remove bone material during insertion of proximal screw member 130 into bone. It should be appreciated that the length of the proximal member 130 may be selected of varying lengths to allow a surgeon to fuse different joints in a foot (not shown).

Figure 3A:
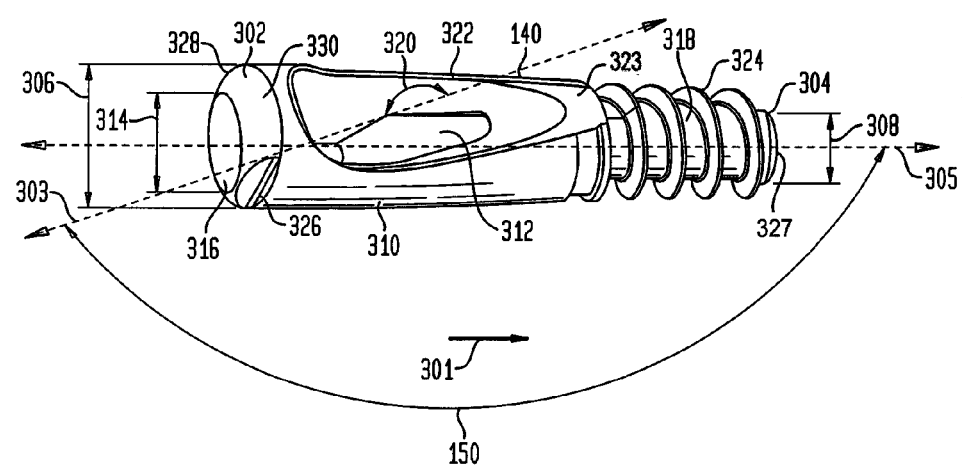
FIG. 3A is a perspective view of a distal member used in the fixation system shown in FIG. 1 according to the preferred embodiment of the present invention.
Figure 3B:
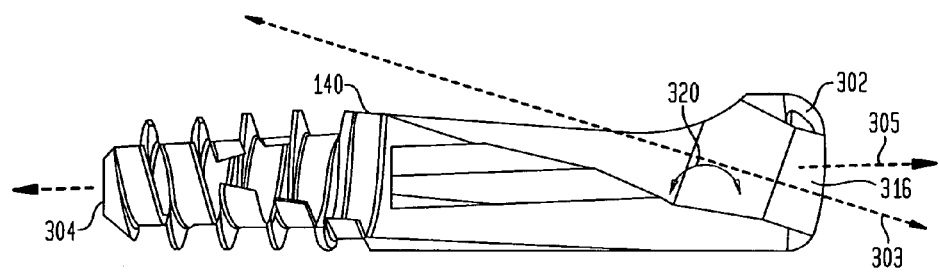
FIG. 3B is a perspective cross-sectional view of the distal member shown in FIG. 3A according to the preferred embodiment of the invention.

As shown in FIGS. 3A-3B, distal member 140 of the preferred embodiment is generally tubular in shape and tapers from a first end 302 to a second end 304 (i.e. end 302 has a diameter 306 that is slightly larger than diameter 308 of end 304). However, in another non-limiting embodiment, distal member 140 has a constant width from first end 302 to second end 304. Further, first end 302 is generally semi-spherical in shape and has an internal circular aperture 316, which traverses end 302 along direction 301 (i.e. end 302 is generally "donut" shaped). Additionally, circular aperture 316 emanates from surface 322, such that portion 310 has a generally tapered aperture 316 provided in portion 310. Circular aperture 316 comprises slope 320 from first end 302 to end 323 of portion 310. Further, aperture 316 is aligned along axis 303, which is offset from horizontal axis 305 of distal member 140. Axis 303 forms an angle 150 with horizontal axis 305 that determines the angle for arch restoration, as shown in FIG. 3A. Angle 150 may be any angle greater than 90 degrees and less than 180 degrees. Tapered aperture 316 when combined with tapered bulbous portion 202, shown in FIG. 2, creates a locked interference fit between proximal member 130 and distal member 140. First end 302 has a plurality of substantially similar grooves 326 and 328, which form an "L-shape" with surface 330 of end 302. Grooves 326 and 328 are provided to receive instrument 120 of fixation system 100, which is later described. In other non-limiting embodiments, other similar instruments may be provided to be received within grooves 326 and 328.

Distal member 140 further comprises a generally smooth portion 310 coupled to end 302. Portion 310 has a generally hexagonal shaped aperture 312, which opens into aperture 316 and which longitudinally traverses through portion 310 in direction 301. In other non-limiting embodiments, a star-shaped aperture, a square-shaped aperture, or any other shaped aperture may be utilized. Circular aperture 316 has a diameter 314 that is slightly larger than external diameter 224 of portion 216 and 206 of proximal screw member 130, with portions 216 and 206 being slidably received within aperture 316 of portion 310. Aperture 316 has a diameter that is smaller than diameter 226 of bulbous portion 202.

Portion 310 of distal member 140 terminates into a second generally cylindrical portion 318 which has a plurality of threads 324, which are circumferentially disposed on the external surface of portion 318. Portion 318 has an internal circular aperture 327 which is longitudinally coextensive with portion 318 in direction 301. Circular aperture 327 aligns with aperture 312 to form a continuous opening from end 302 to end 304.

Figure 4:
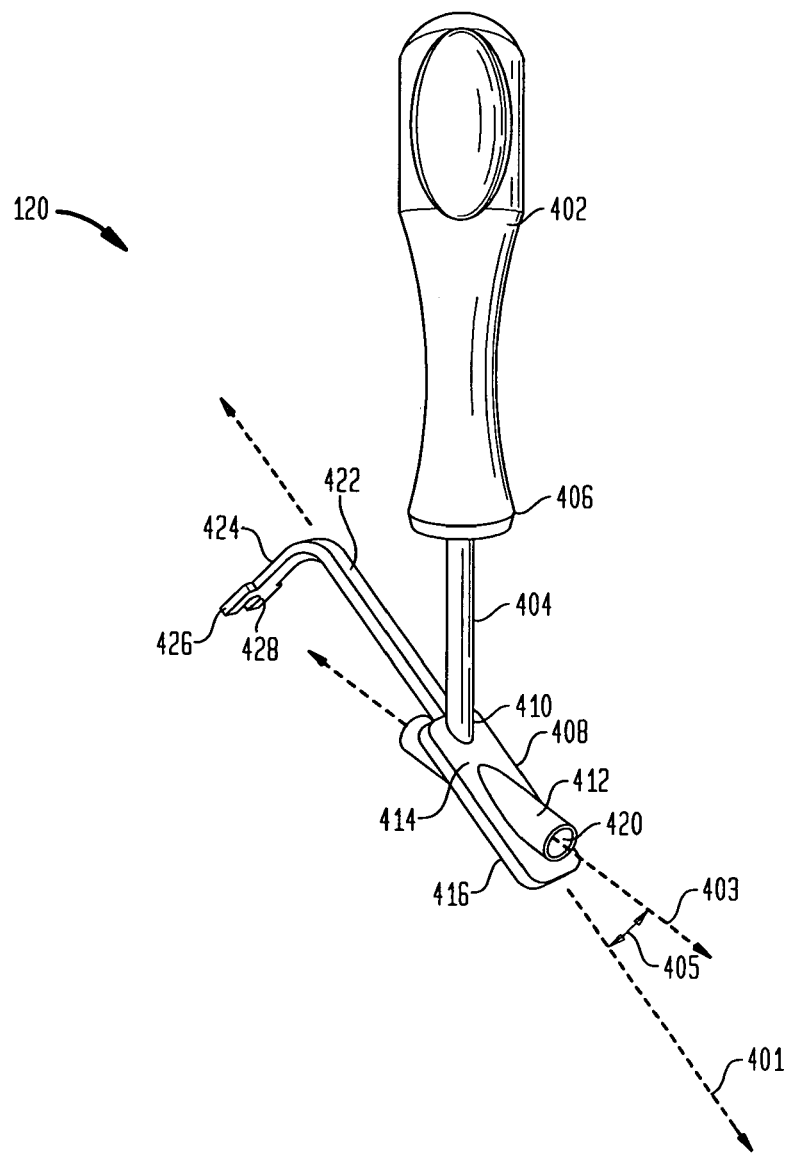
FIG. 4 is a perspective view of the instrument member used in the fixation system shown in FIG. 1 according to the preferred embodiment of the present invention.

As shown in FIG. 4, instrument 120 is illustrated for coupling proximal screw member 130 to distal member 140. Particularly, instrument 120 includes a handle portion 402 coupled to a rod portion 404. Rod portion 404 emanates from handle portion 402 at end 406 and terminates into a rectangular planar portion 408 at end 410. Planar portion 408 is aligned along axis 401 and is fixably coupled to a generally cylindrical tubular portion 412 (i.e., an aiming device). Portion 412 traverses portion 408 from top surface 414 to bottom surface 416. Further, tubular portion 412 is aligned along dissimilar axis 403, forming an angle 405 with axis 401. Also, tubular portion 412 has a through aperture 420 that longitudinally traverses portion 412 along axis 403.

Planar portion 408 is coupled to planar portion 422, with portion 422 having a width slightly smaller than width of portion 408. Portion 422 terminates into a generally "U-shaped" portion 424 with portion 424 being orthogonal to portion 422. Further, portion 424 has a plurality of substantially similar sides 426 and 428 which are provided to be slidably coupled to grooves 326 and 328 of distal member 140.

In operation, sides 426 and 428 of instrument 120 are received in respective grooves 326 and 328 of distal member 140, of FIGS. 3A-3B, thereby slidably coupling distal member 140 to instrument 120. In this position, axis 303 of aperture 316 is aligned along substantially the same axis as axis 403 of instrument 120. Proximal screw member 130 is coupled to distal member 140 by slidably coupling portions 206 and 216 through aperture 420 of tubular portion 412. Tubular portion 412 guides proximal screw member 130 through internal aperture 420 and into aperture 316 on surface 322 and may also guide a Kirschner wire (K wire) or a drill. Proximal screw member 130, of FIG. 2, travels into bone as portions 216 and 206 travel further through aperture 316 at end 302 until bulbous portion 202 is restrained by surface 322 and end 302. Aperture 316, being tapered along axis 303, causes proximal screw member 130 to form an angle 150 with distal member 140, with proximal member 130 being aligned along an axis 303, which is substantially the same axis as axis 403 of tubular portion 412 of instrument 120.

Figure 5:
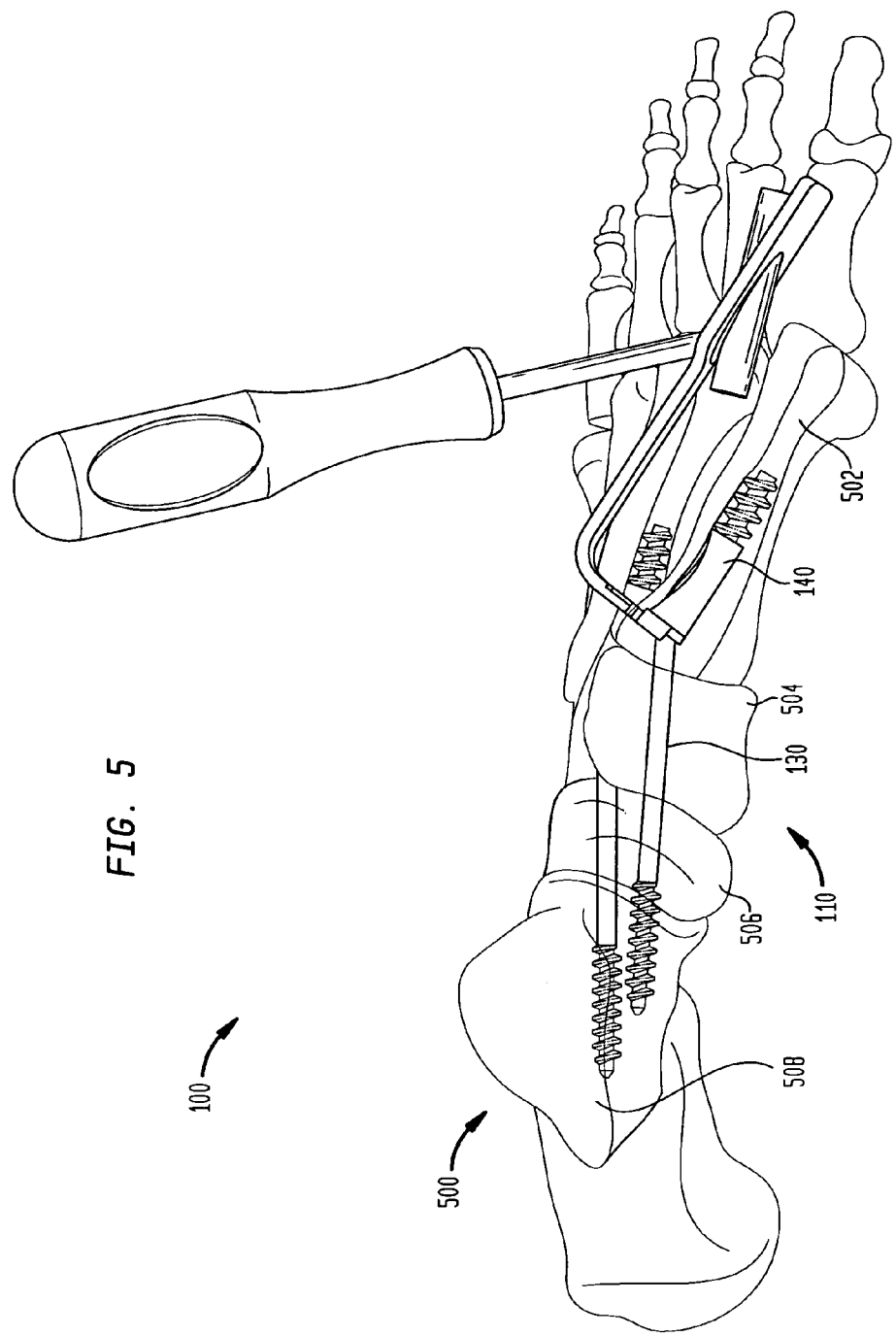
FIG. 5 is a perspective view of the assembled intramedullary fixation assembly inserted into the bones of a patient's foot according to the preferred embodiment of the present invention.
Figure 6:
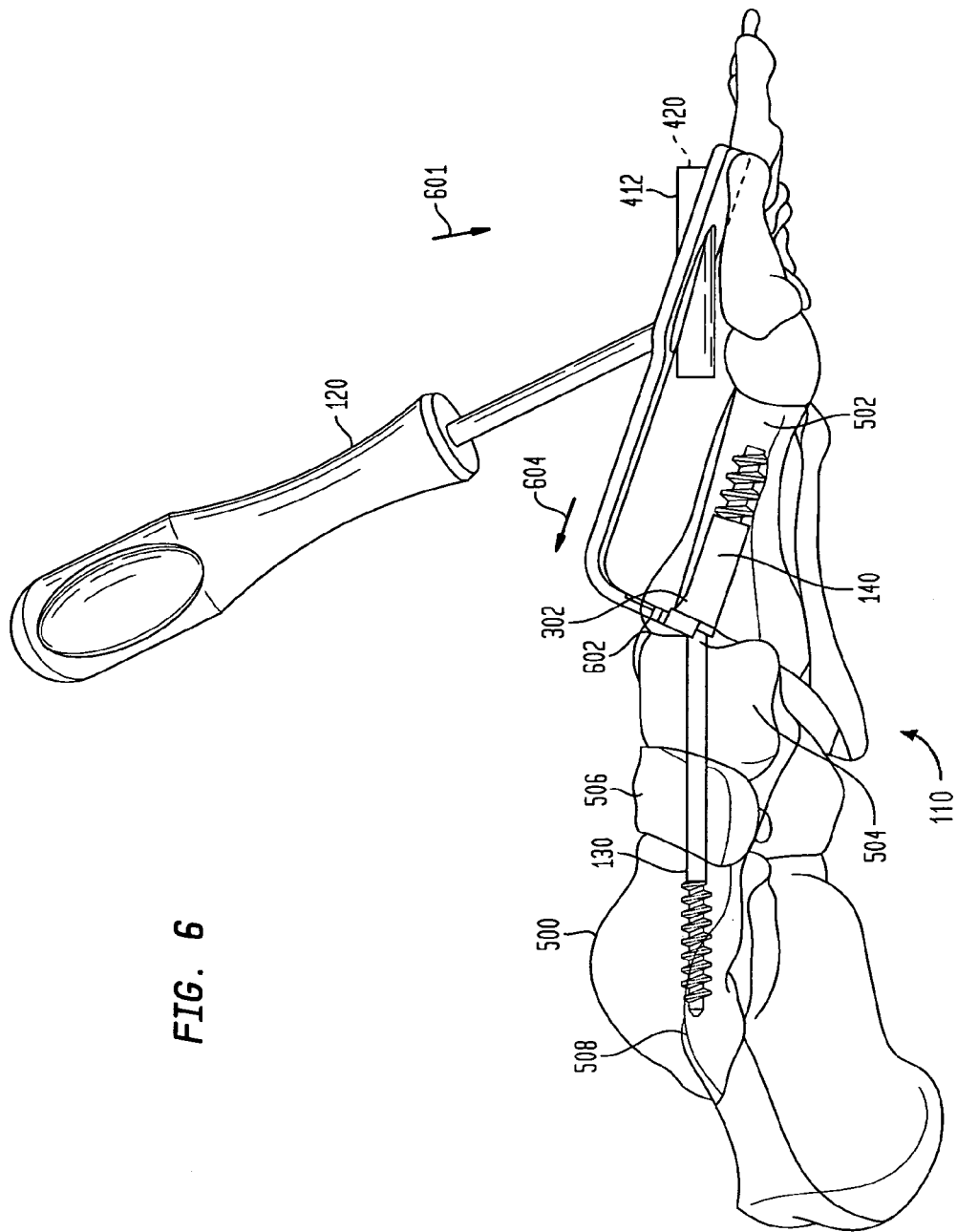
FIG. 6 is a side view of the assembled intramedullary fixation assembly shown in FIG. 5 according to the preferred embodiment of the present invention.
Figure 7:
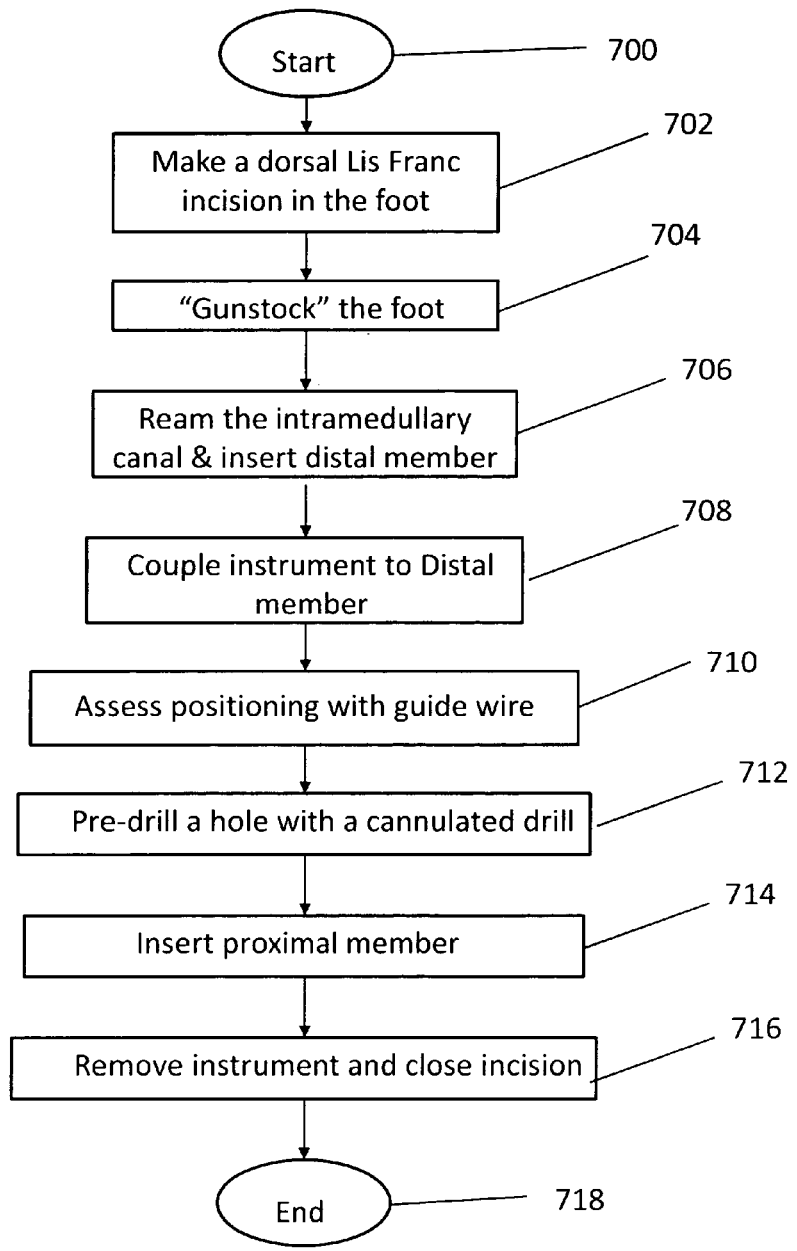
FIG. 7 is a flow chart illustrating the method of coupling the intramedullary fixation assembly shown in FIGS. 1-6 to tarsal and metatarsal bones in a patient's foot according to the preferred embodiment of the present invention.

In operation, and as best shown in FIGS. 5, 6 and 7, the fixation system 100 utilizes the intramedullary fixation assembly 110 for treating and fixating the deteriorated and damaged or fractured bones in the human foot 500. This restores the arch in a human foot 500 by coupling the intramedullary fixation assembly 110 to the human foot 500 of a left leg. In one-non limiting example, and as shown in FIG. 5, the intramedullary assembly 110 is coupled to the medullary canals of the first metatarsal 502, medial cuneiform 504, navicular 506 and talus bone 508. Talus bone 508 makes up part of the ankle joint where the threaded portion 216 of the proximal screw member 130 of the intramedullary assembly 110 is threadably coupled. The medial cuneiform 504 and navicular 506 bones are most affected by Diabetic Charcot foot disorder that causes deterioration and collapse of the arch of the foot 500. It should be appreciated that the intramedullary assembly 110 may be used within each of the five rays, with a ray representing a line drawn from each metatarsal bone to the talus. The angulation in the smaller rays will be smaller than the two rays (i.e., a line from the first and second metatarsal bones to the talus bone). Also, the diameter of distal member 140 will decrease from the large ray to the small ray. In one non-limiting example, the angulation may be any angle greater than 90 degrees and less than 180 degrees. For example, the angle for the first ray may be 150-170 degrees and the angles for the other rays may be 160-175 degrees.

As shown in FIGS. 6 and 7, the intramedullary fixation assembly 110 may be utilized to reconstruct an arch in a mid-foot region of a human foot 500. As shown, the method starts in step 700 and proceeds to step 702, whereby a Dorsal Lis Franc incision (i.e., mid-foot incision) (not shown) is made in foot 500 in order to gain access to the joint. In step 704, the joint capsule is separated by "Gunstocking" foot 500 in direction 601 (i.e., the foot 500 is bent mid-foot) to expose the articular surface 602 and the articulating cartilage is removed. Next, in step 706, the intramedullary canal is reamed and the distal member 140 is inserted into the intramedullary canal (not shown) of the metatarsal 502. In other non-limiting embodiments, the distal member 140 may be inserted by impaction, by press fit, by reaming a hole in the intramedullary canal (not shown) or substantially any other similar strategy or technique. Next, in step 708, the instrument 120 is coupled to the distal member 140 by coupling sides 426 and 428 of instrument 120 to respective grooves 326 and 328. In step 710, initial positioning of the proximal member 130 is assessed with the use of a guide wire through portion 412 (i.e., aiming device). Next, in step 712, a countersink drill is inserted through portion 412 and the proximal cortex is penetrated. In this step, a cannulated drill or guide wire is used to pre-drill the hole through the joints selected for fusion. In step 714, the proximal screw member 130 is inserted over the guide wire and into the distal member 140. Particularly, the proximal member 130 is inserted through tubular portion 412 (i.e., aiming device), causing proximal member 130 to travel through internal longitudinal aperture 420, into distal member 140 and further into bones 504, 506 and 508 until rigid connection with the tapered aperture 316 is made, thereby compressing the joint. In one non-limiting embodiment, a locking element (not shown) such as a plate or a washer is coupled to end 302 of the intramedullary fixation assembly 110 to further secure proximal threaded member 130 to distal member 140. Next, in step 716 the instrument 120 is removed and the dorsal Lis Franc (i.e., mid-foot) incision is closed. The method ends in step 718.

It should be appreciated that a plurality of intramedullary fixation assemblies, such as intramedullary fixation assembly 110, may be inserted into any of the bones of a foot 500 such as, but not limited to the metatarsal, cuneiform, calcaneus, cuboid, talus and navicular bones, in order to restore the natural anatomical shape of the arch of the foot 500. Thus, the fixation system 100, in one non-limiting embodiment, is utilized to couple the intramedullary fixation assembly 110 to the foot 500, which causes the metatarsal 504, medial cuneiform 504, navicular 506 and talus 508 bones to be aligned to the proper anatomical shape of an arch when assembled within foot 500. It should be appreciated that the intramedullary fixation assembly 110 is delivered through a dorsal midfoot incision, thereby reducing the disruption to the plantar tissues and/or the metatarsal heads while at the same time minimizing the tension on the skin. This allows for improved wound closure, reduced operating room time, reduction in the number of incisions required and reduction in the total length of incisions. It should also be appreciated that in other non-limiting embodiments, the intramedullary assembly 110 may be utilized with graft material (i.e., autograft, allograft or other biologic agent).

It should be understood that this invention is not limited to the disclosed features and other similar method and system may be utilized without departing from the spirit and the scope of the present invention.

While the present invention has been described with reference to the preferred embodiment and alternative embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention. It should be appreciated that the present invention is capable of being embodied in other forms without departing from its essential characteristics.

The invention claimed is:

1. An intramedullary fixation assembly for bone fusion, comprising:
    a first screw member comprising a head portion and a first shaft extending along a first longitudinal axis; and
    a second member comprising a second shaft extending along a second longitudinal axis, a bore extending therethrough along a bore axis, a threaded portion at a first end, and a first aperture at a second end, said first aperture diametrically opposed to said first end, wherein said bore extends from said first aperture to an exterior surface on said second member,
    wherein said second longitudinal axis and said bore axis define an angle,
    wherein said first screw member is adapted for coupling to said second member at said angle, and
    wherein each of said first screw member and said second member is adapted for residing substantially within at least one bone.

2. The intramedullary fixation assembly of claim 1, wherein said first screw member comprises a threaded portion diametrically opposed to said head portion.

3. The intramedullary fixation assembly of claim 2, wherein said threaded portion of said first screw member comprises a plurality of bone threads located on an outer surface of said threaded portion of said first screw member.

4. The intramedullary fixation assembly of claim 2, wherein said threaded portion of said first screw member comprises a self-tapping edge adapted for removing bone material.

5. The intramedullary fixation assembly of claim 1, wherein said head portion comprises a taper adapted for providing an interference fit with said second member.

6. The intramedullary fixation assembly of claim 1, wherein said head portion comprises a taper adapted for providing an interference lock with said second member.

7. The intramedullary fixation assembly of claim 1, wherein said first shaft is cannulated.

8. The intramedullary fixation assembly of claim 1, wherein said head portion comprises an aperture adapted for receiving a complementary shaped end of an instrument.

9. The intramedullary fixation assembly of claim 8, wherein said aperture of said head portion comprises a hexagonal shape, a star shape, or a square shape.

10. The intramedullary fixation assembly of claim 1, wherein said threaded portion of said second member contains a plurality of bone threads located on an outer surface of said threaded portion of said second member.

11. The intramedullary fixation assembly of claim 1, wherein said threaded portion of said second member comprises a self-tapping edge adapted for removing bone material.

12. The intramedullary fixation assembly of claim 1, wherein said second member comprises a second aperture extending internally through said second shaft along said second longitudinal axis.

13. The intramedullary fixation assembly of claim 12, wherein said second aperture comprises a hexagonally shaped recess, a star-shaped recess, or a square-shaped recess, wherein each of said hexagonally shaped recess, said star-shaped recess, or said square-shaped recess extends along a partial length of said second aperture.

14. The intramedullary fixation assembly of claim 13, wherein each of said hexagonally shaped recess, said star-shaped recess, or said square-shaped recess is adapted for receiving a complementary shaped end of an instrument.

15. The intramedullary fixation assembly of claim 1, wherein said bore is adapted for receiving said first screw member along said bore axis.

16. The intramedullary fixation assembly of claim 1, wherein said first screw member is adapted for inserting into a first medullary canal of a first bone.

17. The intramedullary fixation assembly of claim 1, wherein said distal second member is adapted for inserting into a second medullary canal of a second bone.

18. The intramedullary fixation assembly of claim 1, wherein said angle is in a range of about 90 degrees to about 180 degrees.

19. A method for compressing bone, comprising the steps of:
    providing a first screw member, the first screw member comprising a head portion and a first shaft extending along a first longitudinal axis; and
    providing a second member, the second member comprising a second shaft extending along a second longitudinal axis, a threaded portion at a first end, a first aperture at a second end, said first aperture diametrically opposite the first end, and a bore extending through the second shaft along a bore axis, wherein the bore extends from the first aperture to an exterior surface on the second member;
    forming a first bore hole in a first bone and forming a second bore hole in a second bone;
    inserting the second member into the first bore hole;

coupling the first screw member to the second member;
inserting the first screw member into the second bore hole; and
applying torque to the head portion to lock the second member to the first screw member, thereby compressing the first bone to the second bone;
wherein the second longitudinal axis and the bore axis define an angle,
wherein the first screw member is adapted for coupling to the second member at the angle, and
wherein the first screw member is adapted for residing substantially within the second bone and the second member is adapted for residing substantially within the first bone.

20. The method of claim 19, wherein the first screw member comprises a threaded portion diametrically opposed to the head portion.

21. The method of claim 20, wherein the threaded portion of the first screw member comprises a plurality of bone threads located on an outer surface of the first threaded portion of the first screw member.

22. The method of claim 20, further comprising removing bone material with a self-tapping edge provided on the threaded portion of the first screw member.

23. The method of claim 19, further comprising forming an interference fit with a taper provided on the head portion and the second member.

24. The method of claim 19, further comprising forming an interference lock with a taper provided on the head portion and the second member.

25. The method of claim 19, wherein the first shaft is cannulated along the first longitudinal axis.

26. The method of claim 19, further comprising receiving a complementary shaped end of an instrument in an aperture of the head portion.

27. The method of claim 26, wherein the aperture of the head portion includes a hexagonal shape, a star shape, or a square shape.

28. The method of claim 19, wherein the threaded portion of the second member comprises a plurality of bone threads located on an outer surface of the threaded portion of the second member.

29. The method of claim 19, further comprising removing bone material with a self-tapping edge provided on the threaded portion of the second member.

30. The method of 19, wherein the second member comprises a second aperture extending internally through the second shaft along the second longitudinal axis.

31. The method of claim 30, wherein the second aperture comprises a hexagonally shaped recess, a star-shaped recess, or a square-shaped recess extending along a partial length of the second aperture.

32. The method of claim 31, wherein each of the hexagonally shaped recess, the star-shaped recess, or the square-shaped recess is adapted for receiving a complementary shaped end of an instrument.

33. The method of claim 19, further comprising receiving the first shaft within the bore along the bore axis.

34. The method of claim 19, wherein the angle is in a range of about 90 degrees to about 180 degrees.

35. A fixation system for compressing bone, comprising:
a first screw member comprising a head portion and a first shaft extending along a first longitudinal axis;
a second member comprising a second shaft extending along a second longitudinal axis, a threaded portion at a first end and a first aperture at a second end, said first aperture being diametrically opposed to said first end, and a bore extending through said second member along a bore axis, wherein said bore extends from said first aperture to an exterior surface on said second member; and
an instrument adapted for coupling said first screw member to said second member;
wherein said second longitudinal axis and said bore axis define an angle,
wherein said first screw member is adapted for coupling to said second member at said angle, and
wherein each of said first screw member and said second member is adapted for residing substantially within at least one bone.

36. The fixation system of claim 35, wherein said proximal first screw member comprises a first threaded portion diametrically opposed to said head portion.

37. The fixation system of claim 36, wherein said threaded portion of said first screw member comprises a plurality of bone threads located on an outer surface of said threaded portion of said first screw member.

38. The fixation system of claim 36, wherein said threaded portion of said first screw member comprises a self-tapping edge adapted for removing bone material.

39. The fixation system of claim 35, wherein said head portion comprises a taper adapted for providing an interference fit with said distal second member.

40. The fixation system of claim 35, wherein said head portion comprises a taper adapted for providing an interference lock with said distal second member.

41. The fixation system of claim 35, wherein said first shaft is cannulated.

42. The fixation system of claim 35, wherein said head portion comprises an aperture adapted for receiving a complementary shaped end of an instrument.

43. The fixation system of claim 42, wherein said first aperture of said head portion comprises a hexagonal shape, a star shape, or a square shape.

44. The fixation system of claim 35, wherein said threaded portion of said second member comprises a plurality of bone threads located on an outer surface of said threaded portion of said second member.

45. The fixation system of claim 35, wherein said threaded portion of said second member comprises a self-tapping edge adapted for removing bone material.

46. The fixation system of claim 35, wherein said second member comprises a second aperture extending internally through said second shaft along said second longitudinal axis.

47. The fixation system of claim 46, wherein said second aperture comprises a hexagonally shaped recess, a star-shaped recess, or a square-shaped recess, wherein each of said hexagonally shaped recess, said star-shaped recess, or said square-shaped recess extends along a partial length of said second aperture.

48. The fixation system of claim 47, wherein each of said hexagonally shaped recess, said star-shaped recess, or said square-shaped recess is adapted for receiving a complementary shaped end of an instrument.

49. The fixation system of claim 35, wherein said first shaft is adapted for residing within said bore along said bore axis.

50. The fixation system of claim 35, wherein said first screw member is adapted for inserting into a first bore hole of a bone.

51. The fixation system of claim 50, wherein said bore hole is located in a cuneiform bone, a navicular bone, or a talus bone in a foot.

52. The fixation system of claim 35, wherein said second member is adapted for inserting into a bore hole of a bone.

53. The fixation system of claim 52, wherein said bore hole is located in a metatarsal bone in a foot.

54. The fixation system of claim 35, wherein said angle is in a range of about 90 degrees to about 180 degrees.

55. An intramedullary fixation assembly for bone fusion, comprising:
   a first screw member comprising a head portion and a first shaft extending along a first longitudinal axis; and
   a second member comprising a second shaft extending along a second longitudinal axis, a bore extending therethrough along a bore axis, a threaded portion at a first end, an aperture at a second end diametrically opposed to said first end, and first and second circumferentially spaced recesses adapted for coupling to an instrument, wherein said first and second recesses are disposed at said second end of said second member;
   wherein said second longitudinal axis and said bore axis define an angle,
   wherein said first screw member is adapted for coupling to said second member at said angle, and
   wherein each of said first screw member and said second member is adapted for residing substantially within at least one bone.

56. An intramedullary fixation assembly for bone fusion, comprising:
   a first screw member comprising a head portion and a first shaft extending along a first longitudinal axis; and
   a second member comprising a second shaft extending along a second longitudinal axis and a bore extending therethrough along a bore axis;
   wherein said second longitudinal axis and said bore axis define an angle,
   wherein said first screw member is adapted for coupling to said second member at said angle, wherein said angle determines an angle for arch restoration, and
   wherein each of said first screw member and said second member is adapted for residing substantially within at least one bone.

57. A method for compressing bone, comprising the steps of:
   providing a first screw member, the first screw member comprising a head portion and a first shaft extending along a first longitudinal axis; and
   providing a second member, the second member comprising a second shaft extending along a second longitudinal axis and a bore extending through the second shaft along a bore axis;
   forming a first bore hole in a first bone and forming a second bore hole in a second bone;
   inserting the second member into the first bore hole;
   coupling an instrument to first and second circumferentially spaced recesses on the second member;
   coupling the first screw member to the second member;
   inserting the first screw member into the second bore hole; and
   applying torque to the head portion to lock the second member to the first screw member, thereby compressing the first bone to the second bone;
   wherein the second longitudinal axis and the bore axis define an angle,
   wherein the first screw member is adapted for coupling to the second member at the angle, and
   wherein the first screw member is adapted for residing substantially within the second bone and the second member is adapted for residing substantially within the first bone.

58. A method for compressing bone, comprising the steps of:
   providing a first screw member, the first screw member comprising a head portion and a first shaft extending along a first longitudinal axis; and
   providing a second member, the second member comprising a second shaft extending along a second longitudinal axis and a bore extending through the second shaft along a bore axis;
   forming a first bore hole in a first bone and forming a second bore hole in a second bone;
   inserting the second member into the first bore hole;
   coupling the first screw member to the second member;
   inserting the first screw member into the second bore hole; and
   applying torque to the head portion to lock the second member to the first screw member, thereby compressing the first bone to the second bone;
   wherein the second longitudinal axis and the bore axis define an angle,
   wherein the first screw member is adapted for coupling to the second member at the angle, and wherein the angle determines an angle for arch restoration, and
   wherein the first screw member is adapted for residing substantially within the second bone and the second member is adapted for residing substantially within the first bone.

59. A fixation system for compressing bone, comprising:
   a first screw member comprising a head portion and a first shaft extending along a first longitudinal axis;
   a second member comprising a second shaft extending along a second longitudinal axis and a bore extending through said second shaft along a bore axis; and
   an instrument adapted for coupling said first screw member to said second member;
   wherein said second longitudinal axis and said bore axis define an angle,
   wherein said first screw member is adapted for coupling to said second member at said angle,
   wherein each of said first screw member and said second member is adapted for residing substantially within at least one bone, and
wherein said second member comprises first and second circumferentially spaced recesses adapted for coupling to said instrument.

60. A fixation system for compressing bone, comprising:
   a first screw member comprising a head portion and a first shaft extending along a first longitudinal axis;
   a second member comprising a second shaft extending along a second longitudinal axis and a bore extending through said second shaft along a bore axis; and
   an instrument adapted for coupling said first screw member to said second member;
   wherein said second longitudinal axis and said bore axis define an angle,
   wherein said first screw member is adapted for coupling to said second member at said angle, wherein said angle determines an angle for arch restoration, and
   wherein each of said first screw member and said second member is adapted for residing substantially within at least one bone.

* * * * *